US00PP22319P3

(12) United States Plant Patent
Lavee et al.

(10) Patent No.: US PP22,319 P3
(45) Date of Patent: Dec. 13, 2011

(54) OLIVE TREE NAMED 'MASEPO'

(50) Latin Name: ***Olea europaea* L.**
Varietal Denomination: MASEPO

(75) Inventors: Shimon Lavee, Rehovot (IL); Benjamin Avidan, Reshon LeZion (IL); Yair Manni, Rosh Haain (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 12/589,970

(22) Filed: Oct. 30, 2009

(65) Prior Publication Data

US 2011/0107477 P1 May 5, 2011

(51) Int. Cl.
*A01H 5/00* (2006.01)

(52) U.S. Cl. ..... Plt./158

(58) Field of Classification Search ..... Plt./158
See application file for complete search history.

(56) References Cited

OTHER PUBLICATIONS

Print-out of registration number and grant date information for corresponding IL PBR application No. 3516/03 granted as Registration No. 2713 on Aug. 26, 2007, published by the Ministry of Agriculture & Rural Development in Israel PBR Gazette No. 72, Jan. 1, 2008-Dec. 30, 2008 (3 pages). http://www.moag.gov.il/NR/rdonlyres/8D0AE3A4-851E-4E58-A239-C70D49E646D6/0/ILgaz72_jan09.pdf.

*Primary Examiner* — Kent L Bell
(74) *Attorney, Agent, or Firm* — Foley & Lardner LLP

(57) ABSTRACT

A new and distinct *Olea europaea* L. olive tree variety named 'MASEPO', particularly characterized by a small to medium-sized tree facilitating hand picking, suitable for intensive orchard growing with harvesting from the ground level with only minimal pruning required, good resistance to *Spilocaea oleagina* and round fruit, with attractive black color when ripe and desirable taste when processed at full black maturation.

3 Drawing Sheets

Latin name of the genus and species of the plant claimed: *Olea europaea* L.

Variety denomination: 'MASEPO'.

BACKGROUND OF THE INVENTION

The present invention relates to a new and distinct variety of an olive tree, botanically described as *Olea europaea* L. of the Oleaceae family, and hereinafter referred to by the variety denomination 'MASEPO'.

The new *Olea europaea* L. 'MASEPO' is a product of a planned breeding program conducted by the inventors, Shimon Lavee, Benjamin Avidan and Yair Manni, in Bet Dagan, Israel. The objective of the breeding program was to develop a new *Olea europaea* L. which is suitable for both green and black pickling, exhibits resistance to *Spilocaea oleagina* (peacock eye leaf disease), requires minimal pruning and facilitates hand-picking.

The new *Olea europaea* L. 'MASEPO' originated as a result of self pollination of the *Olea europaea* L. 'MANZANILLO' (unpatented) made by the inventors in 1990 in Bet Dagan, Israel. The new *Olea europaea* L. 'MASEPO' was observed and selected from the progeny of the stated self-pollination in 1994 by the inventors in a controlled environment in Bet Dagan, Israel.

Asexual propagation of the new *Olea europaea* L. 'MASEPO' by rooting of vegetative cuttings was first performed in the spring of 1995 in Bet Dagan, Israel, and has demonstrated that the combination of characteristics as herein disclosed for the new variety are firmly fixed and retained through successive generations of asexual propagation. The new variety propagates true to type.

BRIEF DESCRIPTION OF THE INVENTION

The following traits have been repeatedly observed and are determined to be characteristics of 'MASEPO' which in combination distinguish this olive tree as a new, unique and distinct variety:

1. A small to medium-sized tree facilitating hand picking;
2. Suitable for intensive orchard growing with harvesting from the ground level with only minimal pruning required;
3. Good resistance to *Spilocaea oleagina*; and
4. Round fruit, with attractive black color when ripe and desirable taste when processed at full black maturation.

In comparison to the unpatented, parental variety, *Olea europaea* L. 'MANZANILLO', the new *Olea europaea* L. 'MASEPO' differs primarily in the traits listed in Table 1.

TABLE 1

Comparison with parent variety.

| Trait | New Variety 'MASEPO' | Female Parent 'MANZANILLO' (unpatented) |
|---|---|---|
| Trunk diameter (measured at 50 cm above ground) | About 41 cm | About 43 cm |
| Tree Height | Up to about 3.2 m | Up to about 4.5 m |

Of the many commercial varieties known to the present inventors, the most similar in comparison to *Olea europaea* L. 'MASEPO' is *Olea eueopaea* L. 'BARNEA' (unpatented). 'MASEPO' differs from 'BARNEA' in the traits described in Table 2:

TABLE 2

Comparison with a well known commercial variety.

| Trait | New Variety 'MASEPO' | Comparison variety 'BARNEA' |
|---|---|---|
| Tree type | Semi-dwarf | Normal |
| Fruit shape | Globose | Elongated |
| Conspicuousness of marbling | Very weak | Weak |
| Time of ripening | Very late | Medium |

BRIEF DESCRIPTION OF THE PHOTOGRAPHS

The accompanying photographs illustrate the overall appearance of the new *Olea europaea* L. 'MASEPO' showing the colors as true as is reasonably possible with colored reproductions of this type. Colors in the photographs may differ slightly from the color values cited in the detailed botanical description, which accurately describe the color of 'MASEPO'.

DETAILED BOTANICAL DESCRIPTION

Figure 1:
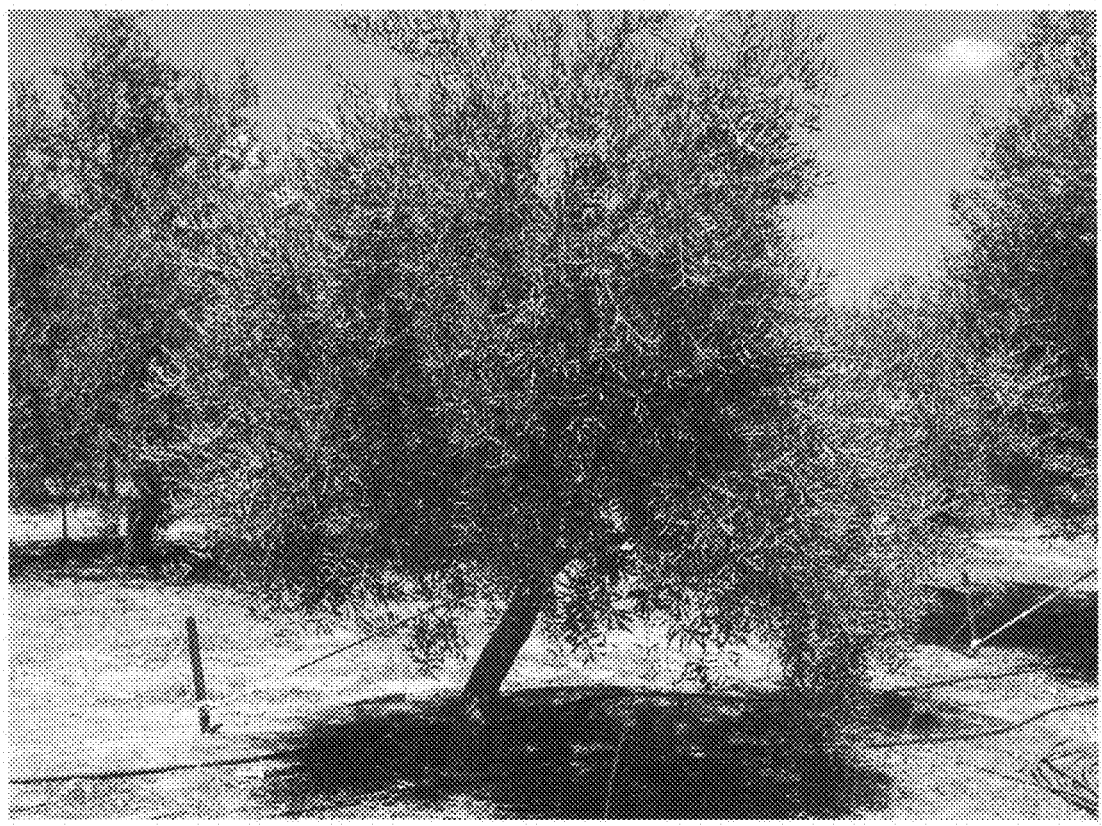
FIG. 1 shows a side view perspective of a typical 10-year-old specimen of 'MASEPO' exhibiting its overall appearance.
Figure 2:
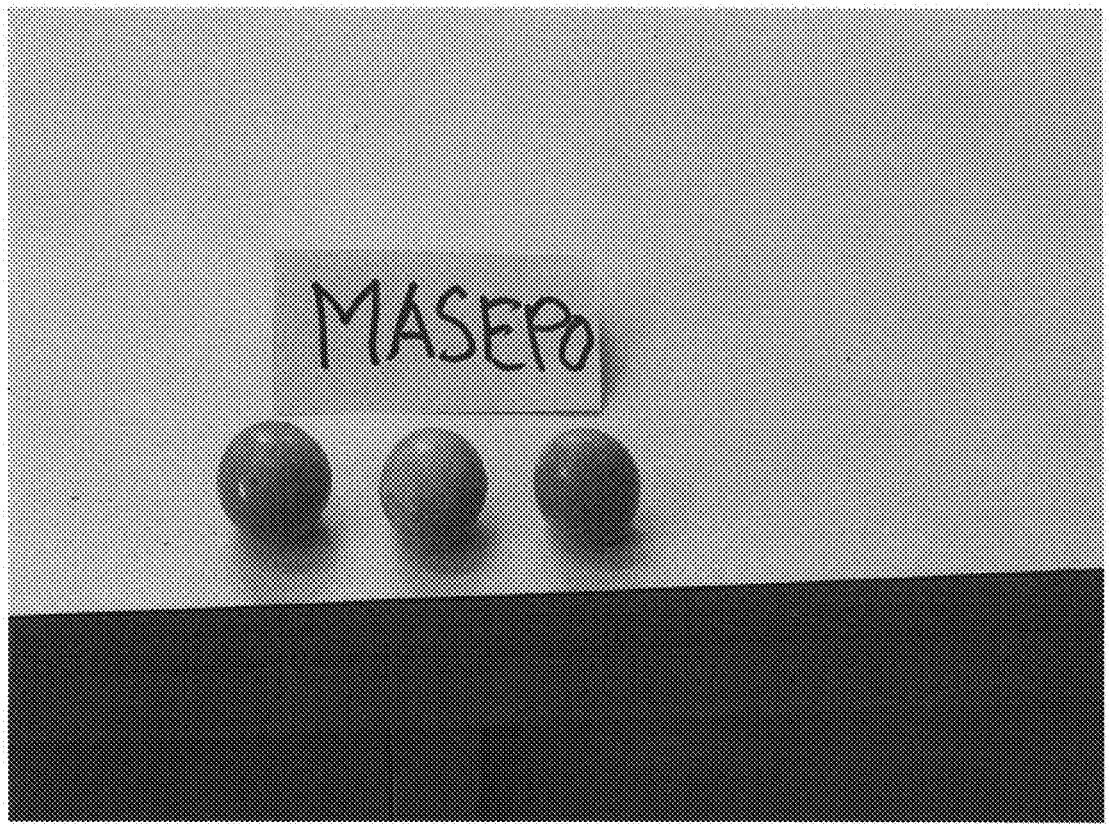
FIG. 2 shows a close-up view of typical unripe, fully grown fruit of 'MASEPO'.
Figure 3:
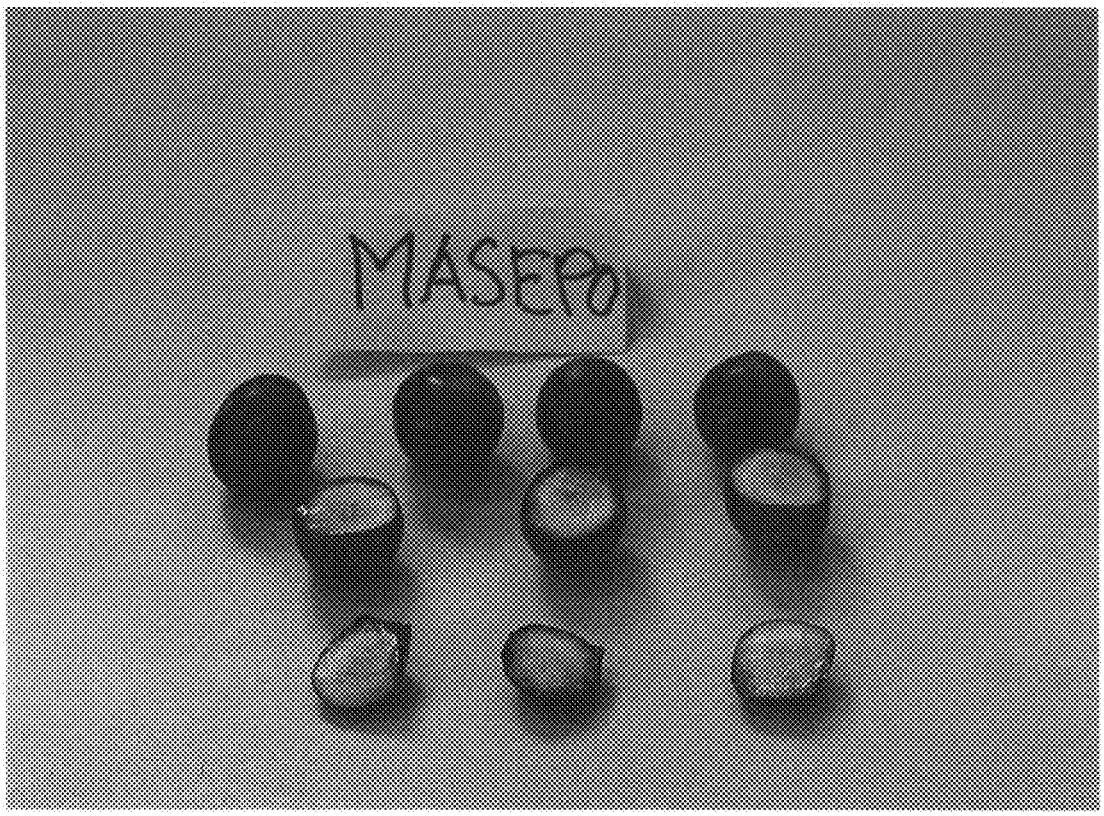
FIG. 3 shows a close-up view of typical ripe, fully grown fruit of 'MASEPO' and it's flesh.

The new *Olea europaea* L. 'MASEPO' has not been observed under all possible environmental conditions. The phenotype of the new variety may vary with variations in environment such as temperature, light intensity, and day length without any change in the genotype of the olive tree.

The aforementioned photographs, together with the following observations, measurements and values describe trees of 'MASEPO' as grown in the olive farm in Bet Dagan, Israel, under conditions which closely approximate those generally used in commercial practice in Israel. Trees of 'MASEPO' are planted at a distance of 4×7 meters in sandy red loam soil at an elevation of about 30 meters above sea level. Trees of 'MASEPO' are irrigated by drip system (about 4 liters per hour) during the summer. Average annual rainfall is about 550 mm, with an average 350 mm of rainfall in winter (December to February). NPK fertilization (9:3:9.50 ppm) is administered through the drip system. Mean diurnal minimum temperature in January is 7.2° C., and mean diurnal maximum temperature in July is 30.8° C.

Unless otherwise stated, the detailed botanical description includes observations, measurements and values based on ten-year-old 'MASEPO' trees grown in the olive farm in Bet Dagan, Israel from 2004 to 2007. Quantitative data are expressed as an average of measurements taken from 10 parts of trees of 'MASEPO'. The measurements of any individual tree, or any group of trees, of the new variety may vary from the stated average.

Color references are made to The Royal Horticultural Society Colour Chart (R.H.S.), 1986 edition, except where general colors of ordinary significance are used. Color values were taken under conditions of full sunlight in Bet Dagan, Israel.

All of the trees of 'MASEPO', insofar as they have been observed, have been consistent in all the characteristics described below.

Classification:

*Botanical.*—*Olea Europaea* L.

Parentage: Self pollination of *Olea europaea* L. 'MANZANILLO' (unpatented)

Propagation:

*Method.*—Rooting of cuttings.

Growing conditions:

*Light intensities.*—Full sunlight.

*Temperature.*—Mean diurnal minimum temperature in January is 7.2° C., and mean diurnal maximum temperature in July is 30.8° C.

*Fertilization.*—NPK fertilization (9:3:9.50 ppm) is administered through the drip system.

*Growth regulators.*—No growth regulators are used.

*Pruning or trimming requirements.*—The olive tree of 'KADESHON' as described is grown without training. When the trees are freely grown, the size and the shape assumed by the plants are not typical of *Olea europaea* L. species.

*Plant.*—Type: semi-dwarf. Growth habit: semi-drooping. Vigor: strong. Height: up to about 3.2 m. Diameter (Spread) of Canopy: about 2.5 m. Diameter of trunk (at 50 cm height): about 41 cm. Attitude of branches: spreading. Density of canopy: medium. Aspect of bark: rough. Bark color: gray RHS 179 B. Lenticels: not visible. Abnormal leaves: absent. Shape of abnormal leaves: Not relevant.

*Main branch.*—Number of main branches per tree: 2 or 3 or 4 resulting from pruning. Length: the length of the branch is up to 3 meters. Diameter: 10-20 cm. Color: gray RHS 197 D. Angle of main branches with axis of the tree: about 45°. Surface slightly rough. Lenticels: not visible.

*One year old shoot.*—Shape in cross section: round. Diameter: 7-9 mm. Color: gray RHS 156 A. Surface: smooth. Lenticels: present. Density of lenticels: sparse. Shape of lenticel: round. Size of lenticel: minuscule. Color of lenticel: gray RHS 196 A.

*Fruiting shoot.*—Color: light grey. Length of node: medium to long 22-38 mm. Feathers (side branching of shoot): medium.

*Leaves.*—Arrangement: the arrangement of the leaves is typical of *Olea europaea* L. species (two opposite leaves per each node).

*Leaf blade.*—Size: small. Ratio length/width: small to medium. Length: 51-62 mm. Width: 9-12 mm. Shape: elliptic. Glossiness: absent. Color of upper side: medium green RHS 146 B. Color of lower side: light yellow green RHS 145 D. Curvature of longitudinal axis of blade: flat. Twisting: absent. Margin: entire. Undulation of margin: none. Shape of apex: acute. Shape of base: acute. Upper surface: smooth. Lower surface: smooth. Pubescence of upper side: glabrous. Pubescence of lower side: glabrous. Color of main vein of upper side: dark green RHS 146 B. Color of main vein of lower side: dark green RHS 146 B.

*Petiole.*—Length: 5-7 mm. Diameter: about 1 mm. Color: light yellow green RHS 145 D.

*Inflorescence.*—Structure: raceme. Shape: elongated. Branching: strong. Axillary flowers: absent. Length: varies up to 15 cm. Diameter: varies up to 5 cm. Number of flowers per inflorescence: numerous. Fruits per inflorescence: about 1.

*Flower bud.*—Shape: obovoid. Size (just before opening): minuscule. Color: light green RHS 142 B. Pubescence: strong. Bud length: about 4 mm. Bud diameter: about 3 mm.

*Flower.*—Diameter: 5-8 mm. Color: white RHS 155 B. Color of pollen: yellow RHS 3 A. Fragrance: mild.

*Corolla segment.*—Number per flower: 4. Length: about 3 mm. Width: about 2 mm. Shape: elliptic. Shape of apex: rounded. Base: fused. Margin: entire. Color of upper side: white RHS 155 B. Color of lower side: white RHS 155 B.

*Calyx lobe.*—Number per flower: 4. Shape: funnel. Length: about 1 mm. Width: less then 1 mm. Shape of apex: acute. Base: fused. Margin: entire. Color of upper side: typical. Color of lower side: typical.

*Pedicel.*—Length: 1-3 mm. Diameter: less then 1 mm. Surface: smooth. Color: very light green RHS 145 D.

*Fruit.*—

*Fruit* (*drupe*).—In the following description, Position A refers to the position in which the fruit shows its largest asymmetry. Position B can be reached from position A by turning 90 degrees along the longitudinal axes in a way that presents the most developed part of the fruit to the observer (according to UPOV rules). Maturity when described: ripe for eating. Size: large. Weight: about 7.6 g. Length: 26-30 mm. Diameter: 24-26 mm. Length/diameter ratio: 1. Shape: globose. Transversal section shape: circular. Green color: RHS 144 A. Color when physiologically ripe: black RHS 202 A. Color of flash (freshly cut): beige RHS 159 A. Conspicuousness of marbling: very weak to weak. Size of mottles: small. Color of mottles: greenish RHS 145 D. Symmetry in position A: weakly asymmetric. Symmetry in position B: symmetrical. Position of maximum diameter: central. Shape of apex in position A: rounded. Shape of apex in position B: rounded. Mucron: absent. Position of pistil scar: central. Shape of base in position A: truncate. Shape of base in position B: truncate. Percentage of stone: about 13.2. Pulp/stone ratio: about 6.57. Pulp/stone detachment: free stone. Fruit suture curvature: not relevant. Oil content for fresh matter% - Percentage of oil in mesocarp (Analyzed at 50% black fruit): 14.4. Percentage of dry weight: 31. Production per tree: about 25 kg. Oleic acid: not recorded. Polyphenol content: not recorded. Organoleptic characteristics: not recorded.

*Stalk.*—Length: 16-25 mm. Thickness: about 1 mm. Color: grey green RHS 146 D. Width of stalk cavity: medium, about 5-6 mm. Shape of stalk cavity: elliptic. Depth of stalk cavity: medium, about 3 mm. Shape of cross section: circular.

*Stone.*—Shape in position A: obovate. Shape in position B: obovate. Symmetry in position A: symmetrical. Symmetry in position B: symmetrical. Shape of cross section: circular. Position of largest cross section: towards apex. Grooving: medium. Distribution of grooves: including apex. Number of grooves on basal end: more than 10. Distribution of grooves on basal end: irregular. Shape of distal end in position A: rounded. Shape of distal end in position B: rounded. Mucron: present. Shape of base in position A: truncate. Shape of base in position B: truncate. Conspicuousness of suture: inconspicuous. Curvature of suture: not relevant. Size: very large. Length: 15-17 mm. Diameter: 11-13 mm. Color when dry: beige RHS 164 C. Weight: about 1.003 g.

*Time of flowering.*—Mid-end April in Bet Dagan, Israel.

*Flowering period.*—About 10 days in Bet Dagan Israel.

*Time of ripening* (*green maturation*).—Mid-August in Bet Dagan Israel.

*Period of ripening.*—About 3 Weeks in Bet Dagan Israel.

Resistance to abiotic factors:

*Cold.*—Observed resistance of down to 0° C. in Bet Dagan, Israel.

Resistance to parasites:

*Spilocaea oleagina.*—'MASEPO' exhibits resistance.

*Pseudomonas savastanoi.*—'MASEPO' has not been tested.

What is claimed is:

1. A new and distinct *Olea europaea* L. olive tree variety named 'MASEPO', as illustrated and described herein.

* * * * *